US00PP12391P2

(12) United States Plant Patent
Zaiger et al.

(10) Patent No.: US PP12,391 P2
(45) Date of Patent: Feb. 5, 2002

(54) PEACH TREE NAMED 'SIERRA RICH'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/824,442

(22) Filed: Apr. 3, 2001

(51) Int. Cl.[7] ..... A01H 5/00
(52) U.S. Cl. ..... Plt./198
(58) Field of Search ..... Plt./198

*Primary Examiner*—Bruce R. Campell
*Assistant Examiner*—Anne Marie Grünberg

(57) ABSTRACT

A new and distinct variety of peach tree (*Prunus persica*), which has the following unique combination of desirable features, that are outstanding in a new variety. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as, pruning, thinning, spraying, irrigation and fertilization.

1. Heavy and regular production of fruit.
2. Fruit with a high degree of attractive red skin color.
3. Fruit with good flavor and eating quality.
4. Fruit with good handling and shipping quality.
5. Fruit holding firm on the tree 7 to 10 days after shipping ripe.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Vista' Peach tree (U.S. Plant Pat. No. 9,549) and 'Zee Lady' Peach tree (U.S. Plant Pat. No. 5,832).

ORIGIN OF THE VARIETY

The present new peach tree (*Prunus persica*) was developed by us in our experimental orchard located near Modesto, Calif. as a first generation cross between 'Zee Lady' Peach (U.S. Plant Pat. No. 5,832) and 'Vista' Peach (U.S. Plant Pat. No. 9,549). We planted and maintained a large group of these first generation trees on their own root system, during which time one seedling, which is the present variety, exhibited the outstanding desirable fruit characteristics described below and was selected in 1992 for asexual propagation and commercialization.

ASEXUAL REPRODUCTION OF THE VARIETY

Asexual reproduction of the new and distinct variety of peach tree was by budding to 'Nemaguard' Rootstock (non-patented), the standard rootstock for peaches in California, as performed by us in our experimental orchard near Modesto, Calif., and shows that reproductions run true to the original tree and all characteristics of the tree and its fruit are established and transmitted through succeeding asexual propagations.

SUMMARY OF THE NEW VARIETY

The new and distinct variety of peach tree is of large size, vigorous upright growth and a productive and regular bearer of large, highly colored, yellow fleshed, freestone fruit with good flavor and eating quality. The fruit is round in shape, has firm flesh with good storage and shipping quality, has the ability to hold firm on the tree 7 to 10 days after maturity (shipping ripe) and in comparison to the 'Zee Lady' Peach (U.S Plant Pat. No. 5,832), its maternal parent, the new variety has large, showy flowers, instead of medium, non-showy flowers, the fruit is similar in appearance, shape and color except the new variety has a smaller pit cavity and is approximately one month earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as true as is reasonably possible in a color representation of this type.

DESCRIPTION OF THE VARIETY

The following is a detailed botanical description of the new variety of peach tree, its flowers, foliage and fruit, as based on observations of 8 year old specimens grown on 'Nemaguard' Rootstock (non-patented), near Modesto, Calif., with color terminology (except those in common terms) in accordance with Reinhold Color Atlas by A. Kornerup and J. H. Wanscher.

Tree:

*Size*.—Large. Normal for most peach varieties.

*Vigor*.—Vigorous; growth of 6 to 7 feet in height the first growing season.

*Growth*.—Upright. As tree matures, weight of fruit tends to spread width of tree. Usually pruned to vase shape.

*Productivity*.—Productive. Fruit set usually two or mor times desired amount for marketable size fruit, thinning and spacing of fruit necessary.

*Form*.—Round headed when mature.

*Bearer*.—Regular. Has had adequate fruit set 6 consecutive years. No alternate bearing observed.

*Fertility*.—Self-fertile.

*Density*.—Medium dense. Pruning to open tree to vase shape, allowing more sunlight to center of tree, which enhances fruit color and improves health of fruit bearing wood.

*Hardiness*.—Hardy in all stone fruit growing areas of California. Winter chilling requirement is approximately 850 hours at or below 45° F.

Trunk:

*Size*.—Large, stocky. Circumference 22 inches measured 14 inches above ground on 8 year old tree. Varies with soil type and fertility, climatic conditions and cultural practices.

*Texture*.—Medium shaggy, increases with age of tree.

*Color*.—Grayish brown to brown (4-F-3) to (4-F-4). Becomes darker with age of tree.

Branches:

*Size*.—Medium. Average circumference 7 inches measured 32 inches above ground. Crotch angle varies between 30 to 40 degrees. Increases with heavey crop.

*Surface texture*.—Smooth on new growth to medium rough on older growth. Varies with age of growth.

*Lenticels*.—Size — small, numerous. Average number 58 within a 4 square inch area. Average length 3/32 inch. Average width 3/64 inch. Color — yellow brown to light brown (5-D-7) to (5-D-8).

*Color*.—First year new growth varies from pale green to pale red (30-A-3) to (10-A-3). Older, mature branches vary from light brown to linoleum brown (5-C-6) to (5-E-7).

Leaves:

*Size*.—Large. Average length 5 inches. Average width 1½ inches.

*Form*.—Lanceolate, tip acuminate, base cuneate.

*Margin*.—Serrate.

*Thickness*.—Medium.

*Surface*.—Upper surface relatively smooth, glabrous. Lower surface — relatively smooth, except for small ridges created by midrib and pinnate venation, glabrous.

*Petiole*.—Average length 7/16 inch. Average width 1/16 inch. Color — grayish green (29-C-6). Grooved longitudinally.

*Glands*.—Size — medium to large. Average length 3/64 inch. Type — reniform. Number varies from 0 to 3, average 2. Located on upper portion of petiole and lower portion of leaf blade. Color — dull red to brownish red (10-C-6) to (11-C-6). Dust particles collected on secretion of sticky fluid causes the glands to become darker in color.

*Color*.—Upper surface — green to deep green (29-F-6) to (29-F-8). Lower surface — light green to spinach green (29-E-6) to (29-E-8).

Flower buds:

*Size*.—Medium. Average length 49/64 inch. Average diameter 27/64 inch. Three days before opening.

*Hardiness*.—Hardy in all stone fruit growing areas of California.

*Form*.—Conical, plump, free.

*Shape*.—Becomes elongated just before opening.

*Pubescence*.—Pubescent.

*Color*.—Pale pink to pink (11-A-3) to (11-A-5).

*Pedicel*.—Size — medium. Average length — 11/64 inch. Average width — 7/64 inch. Color — light green to yellowish green (29-B-6) to (29-C-6).

Flowers:

*Size*.—Large, showy. Average height 15/16 inch. Average diameter 1 49/64 inch.

*Petals*.—Number — five, alternately positioned with sepals. Shape — orbicular, narrows at point of attachment. Edge of outer surface varies from smooth to scalloped. Average length 55/64 inch. Average width 13/16 inch. Color — pale pink to pink (11-A-3) to (11-A-5). Color fades with age of flower.

*Sepals*.—Size — medium. Average length — 15/64 inch. Average width — 3/16 inch. Number — five, alternately arranged to petals. Color — lower surface, dull grayish red (11-B-4). Color fades with age of flower, pubescent surface. Upper surface — grayish green (1-D-5) fades as flower ages, glabrous surface.

*Stamens*.—Number per flower 37 to 45, average 41. Average height — 9/16 inch. Filament color — white (1-A-1). Filament length — 17/32 inch. Anther color — madder red (11-B-8). Exceeds height of stigma approximately 3/64 inch.

*Pollen*.—Present. Self-fertile. Color — light yellow to butter yellow (3-A-5) to (4-A-5).

*Pistil*.—Number — usually one, varies from 1 to 2. Average length 47/64 inch. Color — light grayish yellow (3-B-5), fades to nearly white as flower ages. Pubescent surface.

*Fragrance*.—Slight, sweet.

*Blooming period*.—Date of First Bloom Mar. 1, 2000. Date of Petal Fall Mar. 10, 2000. Varies slightly with climatic conditions.

*Color*.—Light pink to pink (11-A-3) to (11-A-5).

*Pedicel*.—Average length — 11/64 inch. Average width — 7/64 inch. Color — light green to yellowish green (29-B-6) to (29-C-6).

Fruit:

*Maturity when described*.—Firm ripe.

*Date of first picking*.—Jun. 24, 2000.

*Date of last picking*.—Jun. 28, 2000. Varies slightly with climatic conditions.

*Size*.—Average diameter axially 2⅞ inches. Average transversely in suture plane 2⅞ inches. Average weight 196 grams. Average weight varies slightly with fertility of the soil, amount of thinning and climatic conditions.

*Form*.—Globose.

*Suture*.—Very shallow, extends from base to apex.

*Ventral surface*.—Smooth, very narrow suture line.

*Apex*.—Nearly rounded, only slight broad apical projection.

*Base*.—Retuse.

*Cavity*.—Rounded to slightly elongated in suture plane. Average depth 7/16 inch. Average breadth 1 inch.

Stem:

*Size*.—Average length 7/16 inch. Average diameter ⅛ inch, enlarged at point of fruit attachment.

*Color*.—Grayish yellow to olive yellow (2-C-6) to (2-B-6).

Flesh:

*Ripens*.—Evenly.

*Texture*.—Firm, meaty.

*Fibers*.—Few, small, tender.

*Firmness*.—Firm, similar to the firmness of 'Zee Lady' Peach.

*Aroma*.—Slight.

*Amydgalin*.—Undetected.

*Eating quality*.—Good.

*Flavor*.—Good, good balance between sugar and acid.

*Juice*.—Moderate, enhances flavor.

*Brix*.—9.6°. Varies with number of fruit per tree and climatic conditions.

*Color*.—Light yellow to yellow (3-A-4) to (3-A-6). Pit cavity varies from pale red to light red (10-A-3) to (10-A-5). Slight bleeding from pit cavity into flesh around stone.

Skin:

*Thickness*.—Medium, tough, shows minimal scarring or tearing during picking and packing trials.

*Texture*.—Medium.

*Tendency to crack*.—None.

*Color*.—Light yellow to yellow ground color, overspread with coral red to madder red (9-B-7) to (10-B-7). Small elongated areas of ground color partially exposing a lighter pattern.

*Pubescence*.—Pubescent, short, moderate amount.

*Tenacity*.—Tenacious to flesh.

*Astringency*.—None.

Stone:

*Type*.—Freestone. Very slight adherence of flesh in small areas.

*Size*.—Large. Average length 1⅜ inches. Average width 1 inch. Average thickness ⅝ inch.

*Form*.—Obovoid.

*Base*.—Usually flat, varies from flat to round.

*Apex*.—Cuspidate. Average length — 7/64 inch.

*Surface*.—Irregularly furrowed toward apex, pitted toward base. Pits vary from round to elongated. One long furrow on each side of suture, extending from base to apex. Narrow ridges vary in length, with rough surfaces.

*Sides*.—Vary from equal to unequal. Some stones have one side extending further from suture plane.

*Tendency to split*.—None.

*Color*.—Varies from reddish brown to brownish red (8-C-6) to (8-D-6) when dry.

Use: Dessert. Market — local and long distance.

Keeping quality: Good, held firm in cold storage for 2 weeks at 38 to 42° F. without internal breakdown of flesh or appreciable loss of eating quality.

Shipping quality: Good, fruit showed minimal scarring or bruising of skin or flesh during packing or shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, which is of large size, vigorous upright growth, and a regular and heavy producer of large, freestone fruit with good flavor and eating quality; the fruit is further characterized by having firm flesh with good shipping and storage quality, having an attractive red skin color and in comparison to the 'Zee Lady' Peach (U.S. Plant Pat. No. 5,832), its maternal parent, the new variety is similar in shape and color, but has a smaller pit cavity and is approximately one month earlier in maturity.

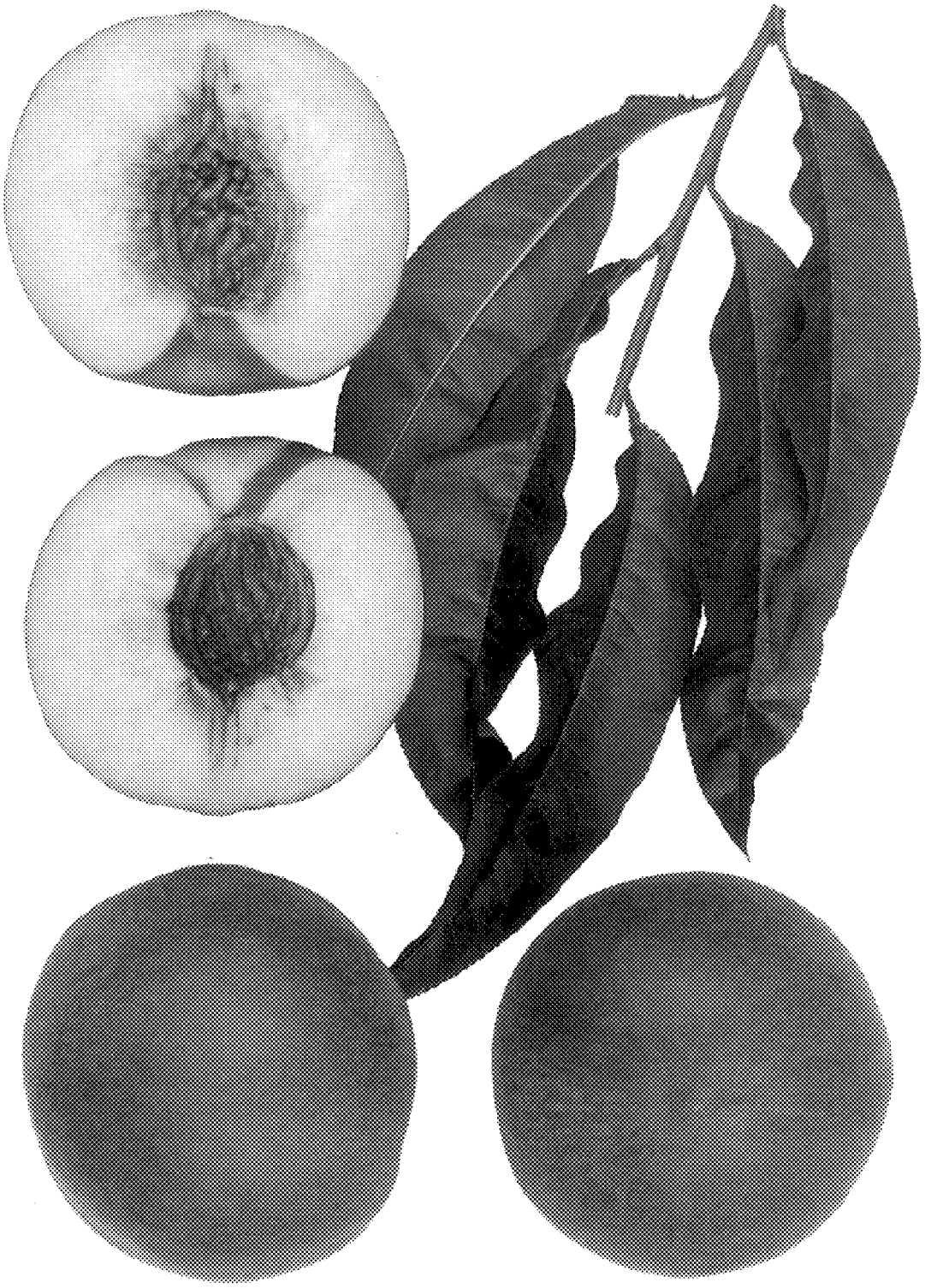

* * * * *